United States Patent
Ottonello et al.

(10) Patent No.: US 9,296,830 B2
(45) Date of Patent: *Mar. 29, 2016

(54) PROCESS FOR RECOVERING SUGARS FROM A PRETREATMENT STREAM OF LIGNOCELLULOSIC BIOMASS

(75) Inventors: Piero Ottonello, Genoa (IT); Simone Ferrero, Tortona (IT); Paolo Torre, Arenzano (IT); Francesco Cherchi, Novi Ligure (IT); Danilo Defaveri, Novi Ligure (IT); Luis Oriani, Anagni (IT)

(73) Assignee: Beta Renewables, S.p.A., Tortona (AL) (IT)

(*) Notice: Subject to any disclaimer, the term of this patent is extended or adjusted under 35 U.S.C. 154(b) by 391 days.

This patent is subject to a terminal disclaimer.

(21) Appl. No.: 13/817,869

(22) PCT Filed: Sep. 29, 2011

(86) PCT No.: PCT/IB2011/054294
§ 371 (c)(1),
(2), (4) Date: Feb. 20, 2013

(87) PCT Pub. No.: WO2012/042498
PCT Pub. Date: Apr. 5, 2012

(65) Prior Publication Data
US 2013/0158253 A1    Jun. 20, 2013

(30) Foreign Application Priority Data
Sep. 29, 2010   (IT) .................................. TO10A0794

(51) Int. Cl.
*D21B 1/36* (2006.01)
*C08B 37/00* (2006.01)
(Continued)

(52) U.S. Cl.
CPC .............. *C08B 37/0057* (2013.01); *C08H 8/00* (2013.01); *C12P 19/02* (2013.01); *C13K 1/02* (2013.01); *C13K 13/002* (2013.01);
(Continued)

(58) Field of Classification Search
CPC .............. D21B 1/02; D21B 1/12; D21B 1/36; C08B 37/0057; C08H 8/00; C12P 2201/00; C07C 53/08; C13K 1/02; C13K 13/002
See application file for complete search history.

(56) References Cited

U.S. PATENT DOCUMENTS 4,152,197 A * 5/1979 Lindahl et al. .................. 162/19
4,908,067 A * 3/1990 Just ................................ 127/37
(Continued)

FOREIGN PATENT DOCUMENTS

| WO | 9814270 A1 | 4/1998 |
| WO | 00/61858 A1 | 10/2000 |
| WO | 01/32715 A1 | 5/2001 |
| WO | WO03/013714 * | 2/2003 |
| WO | 2009/108773 A2 | 9/2009 |

OTHER PUBLICATIONS

International Search Report (Jan. 2012).
(Continued)

*Primary Examiner* — David M Brunsman
(74) *Attorney, Agent, or Firm* — Edwin A. Sisson, Attorney at Law, LLC; Jeffrey J. Banyas

(57) ABSTRACT

This specification discloses an improved method for conducting the removal of C5 xylan based sugars from biomass. The improved method involves a series of soakings and washings of the biomass as opposed to conducting one soaking and washing step.

10 Claims, 2 Drawing Sheets

(51) Int. Cl.
| | |
|---|---|
| C13K 1/02 | (2006.01) |
| C13K 13/00 | (2006.01) |
| C12P 19/02 | (2006.01) |
| D21B 1/02 | (2006.01) |
| D21B 1/12 | (2006.01) |
| D21C 1/02 | (2006.01) |
| C08H 8/00 | (2010.01) |

(52) U.S. Cl.
CPC .............. *C13K 13/007* (2013.01); *D21B 1/02* (2013.01); *D21B 1/12* (2013.01); *D21B 1/36* (2013.01); *D21C 1/02* (2013.01); *C12P 2201/00* (2013.01)

(56) References Cited

U.S. PATENT DOCUMENTS

| | | | | |
|---|---|---|---|---|
| 5,503,996 | A | * | 4/1996 | Torget et al. ................. 435/105 |
| 6,022,419 | A | * | 2/2000 | Torget et al. .................... 127/37 |
| 8,123,864 | B2 | * | 2/2012 | Christensen et al. ............ 127/37 |
| 8,460,473 | B2 | * | 6/2013 | Christensen et al. ............ 127/37 |
| 9,102,856 | B2 | * | 8/2015 | Cherchi .................... C09K 3/00 |
| 2008/0057555 | A1 | * | 3/2008 | Nguyen ......................... 435/165 |
| 2010/0041119 | A1 | * | 2/2010 | Christensen et al. .......... 435/162 |
| 2012/0104313 | A1 | * | 5/2012 | Garbero et al. ........... 252/182.12 |
| 2013/0168602 | A1 | * | 7/2013 | Cherchi et al. ........... 252/182.12 |

OTHER PUBLICATIONS

Wingren et al., "Process Considerations and Economic Evaluation of Two-Step Steam Pretreatment for Production of Fuel Ethanol from Softwood", Biotechnol. Prog., Aug. 26, 2004, pp. 1421 to 1429, vol. 20, American Chemical Society and American Institute of Chemical Engineers.

Rydholm, Sven A., "Pulping Processes", 1965, pp. 410 to 412, Interscience Publishers.

Ramos, Luis Pereira, "The Chemistry Involved in the Steam Pretreatment of Lignocellulosic Materials", Quim. Nova, May 15, 2003, pp. 863 to 871, vol. 26, No. 6.

Zhou et al., "Effect of Hot Water Pretreatment Severity on the Degradation and Enzymatic Hydrolysis of Corn Stover", Transactions of the ASABE, 2010, pp. 1929 to 1934, vol. 53(6), American Society of Agricultural and Biological Engineers.

Olofsson et al., "A short review of SSF—an interesting process option for ethanol production from lignocellulosic feedstocks", Biotechnology for Biofuels, May 1, 2008, pp. 1 to 14, vol. 1:7.

Chornet et al., "Phenomenological Kinetics and Reaction Engineering Aspects of Steam/Aqueous Treatments", Proceedings of the International Workshop on Steam Explosion, Oct. 20-21, 1988, pp. 21 to 58, CRC Press.

Bobleter et al., "Steam Explosion—Hydrothermolysis—Organosols a Comparison", Proceedings of hte International Workshop on Steam Explosion, Oct. 20-21, 1988, pp. 59 to 82, CRC Press.

Overend et al., "Fractionation of lignocellulosics by steam-aqueous pretreatments", Phil. Trans. R. Soc. Lond., 1987, pp. 523 to 536, vol. 321, Great Britain.

Supantamart et al., "Effect of Steam Explosion on Chemical Compositions of Biomass from *Eucalyptus* and *Acacia*", The 3rd International Conference on Fermentation Technology for Value Added Agricultural Products, 2008, pp. 1 to 6.

Fransson et al., "Final Report Goal 1 Southern wood counties", Etek Ethanol technique, pp. 1 to 20.

"Development of ethanol processes in Ornskoldsvik", pp. 1 to 6. (Nov. 2007).

* cited by examiner

PROCESS FOR RECOVERING SUGARS FROM A PRETREATMENT STREAM OF LIGNOCELLULOSIC BIOMASS

PRIORITY AND CROSS REFERENCES

This patent application claims the priority from PCT/IB2011/054294 filed on 29 Sep. 2011 which claims priority from Italian Patent Application Number TO2010A000794 filed on 29 Sep. 2010, the teachings of both of which are incorporated in their entirety.

BACKGROUND

In the biomass field converting lignocellulosic biomass to ethanol is a common practice. If the biomass is a polysaccharide-containing biomass and it is lignocellulosic, a pre-treatment or soaking is often used to ensure that the structure of the lignocellulosic content is rendered more accessible to the enzymes, and at the same time the concentrations of harmful inhibitory by-products such as acetic acid, furfural and hydroxymethyl furfural are usually high and present problems in further processing.

In general terms the more severe the treatment, the more accessible are the cellulosic contents of the material. The severity of the steam explosion is known in the literature as Ro, and is a function of time and temperature expressed as $$Ro = t \times e^{[(T-100)/14.75]}$$

with temperature, T, expressed in Celsius and time, t, expressed in common units. The formula is also expressed as Ln (Ro), namely $$Ln(Ro) = Ln(t) + [(T-100)/14.75].$$

It is generally considered that a high Ro value is associated with a high number of unwanted by-products which inhibit the hydrolysis and fermentation of the biomass, such as furfural.

There exists therefore, the need to have a severe process with a high overall Ro which at the same time produces a product with low furfural and high sugar yields.

SUMMARY

Disclosed in this specification is a process for the soaking of lignocellulosic biomass, comprising the steps of: A) introducing a lignocellulosic biomass feedstock into a first soaking zone, B) soaking the lignocellulosic biomass feedstock in the presence of a liquid or vapor of the liquid for a first time and a first temperature correlating to a first severity of the soaking conditions creating a first liquid comprised of at least one compound selected from the group consisting of acetic acid, glucose, xylose and soluble oligomers thereof, C) separating at least a portion of the first liquid comprised of the at least one compound selected from the group consisting of acetic acid, glucose, xylose and soluble oligomers thereof from the biomass of the first soaking, D) introducing the biomass of the first soaking zone into a second soaking zone in the presence of a liquid for a second time and a second temperature correlating to a second severity of the soaking conditions creating a second liquid comprised of at least one compound selected from the group consisting of acetic acid, glucose, xylose and soluble oligomers thereof wherein the second severity is greater than first severity, E) separating at least a portion of the second free liquid comprised of the at least one compound selected from the group consisting of acetic acid, glucose, xylose and soluble oligomers thereof from the biomass of the second soaking.

It is further disclosed to have an third soaking and washing step by introducing the biomass from the second soaking zone into a third soaking zone in the presence of a liquid for a third time and at a third temperature range correlating to a third severity of the soaking conditions creating a third liquid comprised of at least one compound selected from the group consisting of acetic acid, glucose, xylose and soluble oligomers thereof wherein the third severity is greater than second severity, separating at least a portion of the third liquid comprised of at least one compound selected from the group consisting of acetic acid, glucose, xylose and soluble oligomers thereof from the biomass of the third soaking.

It is further disclosed that the soaking and washing may be conducted in a series vessel, the same vessel or piece of equipment, and that the soaking zones may be situated on top of each other or side by side. It is also disclosed that the process may be continuous or batch.

DETAILED DESCRIPTION

Figure 1:
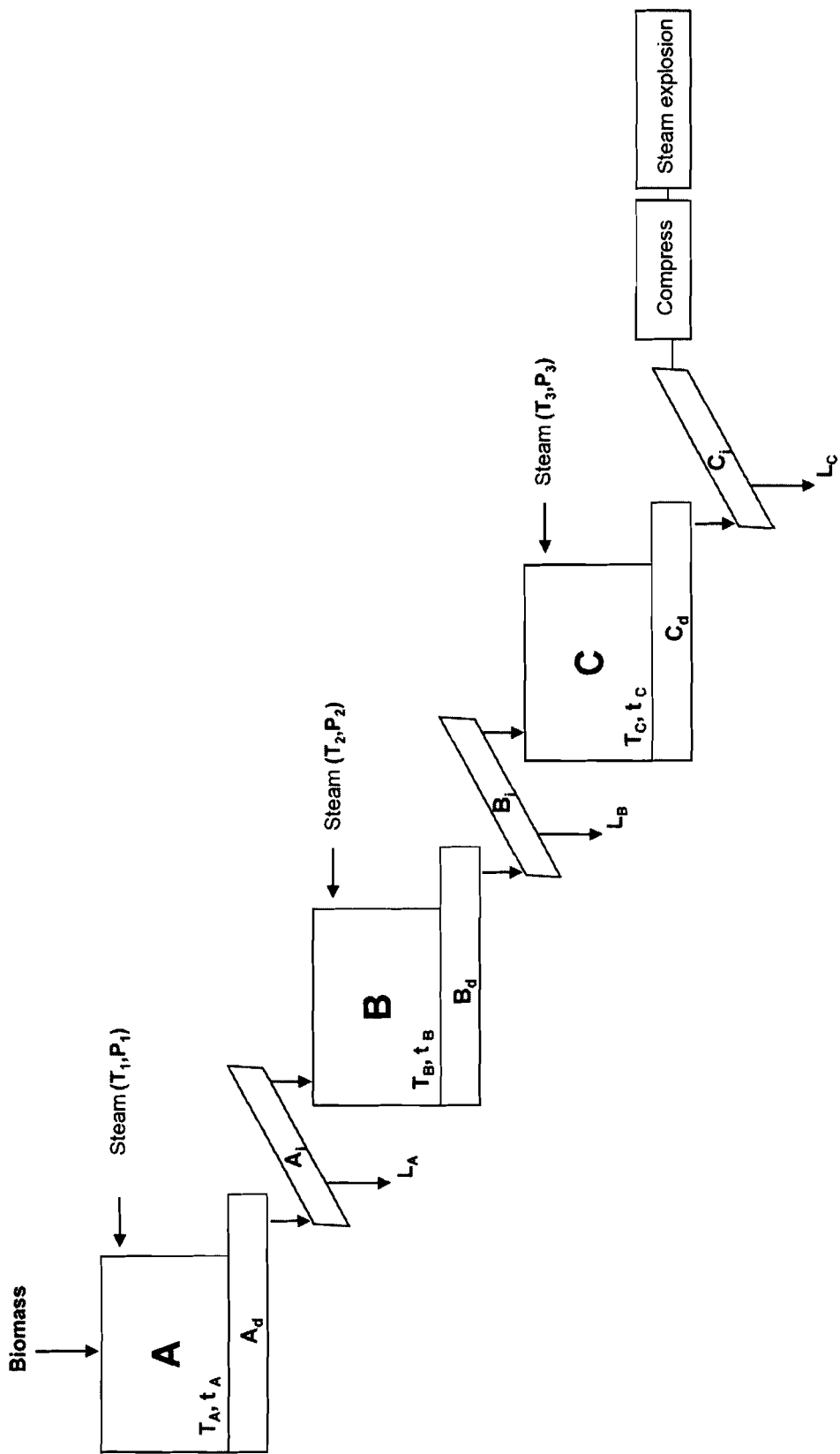
FIG. 1 is a schematic of a first embodiment of the process.

Disclosed in this description is the discovery that when the treating of biomass, in particular lignocellulosic biomass, is conducted in a series of soaking/hydrolysis steps the resulting over-all severity may be very high, indicative of the long time at temperatures during the various phases, but the amount of product recovered is substantially higher than would be expected.

The concept is demonstrated in the following working example with severity being determined by the formula:

$$Ro = t \times e^{[(T-100)/14.75]}$$

with temperature, T, expressed in Celsius and time, t, expressed in common units, in the case below minutes.

The formula is also expressed as Ln (Ro), namely $$Ln(Ro) = Ln(t) + [(T-100)/14.75].$$

When the steps are taken in series, the total severity is the sum of the individual Ro for each soaking step.

The soaking procedure itself is known in the art, which is to place the lignocellulosic biomass having a cellulose content of at least 5% by weight of the dry matter, and preferably at least 10% by weight of the dry matter of the biomass into a soaking zone or reactor, and introduce a vapor, usually steam and maintaining the biomass at a temperature for a set amount of time. Steam is added to the soaking reactor at an exemplary rate of 0.5 kg stm/1 kg biomass feedstock to 10 kg stm/1 kg biomass feedstock, depending upon the severity chosen. Instead of adding steam liquid water can be added and heated up to the those conditions. The soaking zone holds the biomass in the presence of steam and water for approximately 30 minutes to 3 hours or longer, again depending upon the severity desired. The soaking temperature can be in the range 100° C. to 210° C., or even higher, but with diminishing returns. After soaking, the solids/liquid/steam mixture is discharged into an inclined reactor, at typically the same pressure of the soaking reactor. At this point liquid is removed via a discharge screw and into the inclined reactor. The solid biomass is carried up the inclined reactor with the cooled condensate or even added water flowing countercurrent to the solid flow and removing free liquid with dissolved xylans and xylan derivatives.

Comparative Examples CE-A and CE-C
(See Table 2)

In CE-A, a lignocellulosic biomass was soaked at the indicated temperature for the time indicated in Table 1 (SOAKING CONDITIONS). The calculated severity for this step was 20. This single step recovered only 6.94% of the Xylans present in the feed stream. 87.89% remained in the solids, and 5.17% were lost, meaning they were converted to a series of unwanted by-products.

In CE-C, the same feedstock was soaked at the conditions indicated in Table 1, for a severity of 6802, dramatically more severe than the conditions of CE-A. In this single step, 65.05% of the xylans remained in the solids, and 18.92% were recovered in the liquid, but 16.03% of the xylans were lost to by-products.

TABLE 1

SOAKING CONDITIONS

| ID | Temperature (° C.) T | time (min) t | Severity Ro = $t \times e^{[(T-100)/14.75]}$ |
|---|---|---|---|
| A, and CE-A | 100 | 20 | 20 |
| B, | 140 | 30 | 452 |
| C, and CE-C | 180 | 30 | 6802 |

TABLE 2

COMPARATIVE EXAMPLES

| ID | Severity Ro | Xylan in Solid Stream (% of Feed Stock Xylan in Solid Stream) | Xylan in Liquid Stream (% of Feed Stock Xylan in Liquid Stream) | Xylan Lost (% of Feed Stock Xylan not in Solid or Liquid Stream) |
|---|---|---|---|---|
| CE-A | 20 | 87.89 | 6.94 | 5.17 |
| CE-C | 6802 | 65.05 | 18.92 | 16.03 |

In working example 2 (see Table 3), Step CE-A was performed, the liquid removed, followed by step CE-C. As can be seen by the data, the amount of xylan recovered in the liquid stream was slightly lower than expected (the amount recovered from the direct addition of CE-A and CE-C).

Unexpectedly, the amount of xylan lost to by-products was only 11.68% as opposed to the 16.03% lost in single Step CE-C. As the solids after soaking are usually passed on to a steam explosion and enzymatic hydrolysis, the xylan remaining in the solid are available for further recovery.

Working example 2 combined the conditions of soaking step A, washed, and followed by soaking step C.

In working example 3, a step having a severity in between A and C was added, named B. So working example 3, is the lignocellulosic biomass soaked at conditions A, with the liquid stream removed. The remaining solid is then processed at condition B, with the liquid removed. The remaining solid is then processed at conditions C and the liquid removed. As can be seen in Table 3—Working Examples, less xylan were lost than compared to single step C and 36.97% of the xylan were solubilized in the liquid, with 47.91% remaining in the solid stream.

TABLE 3

WORKING EXAMPLES

| ID | Severity Ro | Xylan in Solid Stream (% of Feed Stock Xylan in Solid Stream) | Xylan in Liquid Stream (% of Feed Stock Xylan in Liquid Stream) | Xylan Lost (% of Feed Stock Xylan not in Solid or Liquid Stream) |
|---|---|---|---|---|
| WE-1 A + B | 472 | 76.77 | 13.25 | 9.98 |
| WE-2 A + C | 6822 | 66.50 | 21.82 | 11.68 |
| WE-3 A + B + C | 7273 | 47.91 | 36.97 | 15.12 |

This evidence demonstrates the improved efficiency of conducting the soaking and washing steps in a sequential manner. This process could be done in a series of vessels as depicted in FIG. 1, where the severity, in either temperature or time is progressively increased from one vessel to another.

Referring to FIG. 1, the soaking zones A, B, and C are oriented in series. They are maintained at their respective temperature. In the case of Zone A, the steam entering the soaking zone A is at a Temperature $T_1$ and Pressure $P_1$, with biomass being kept in the zone at temperature $T_A$ and for a time, $t_A$. The biomass moves through a discharge screw, $A_d$, flowing into an inclined reactor ($A_i$) with liquid $L_A$ being removed.

The biomass which has been soaked once, moves into the next soaking zone, Zone B, being characterized similarly as Zone A. In the case of Zone B, the steam entering the soaking zone B is at a Temperature $T_2$ and Pressure $P_2$, with biomass being kept in the zone at temperature $T_B$ and for a time, $t_B$. The biomass moves through a discharge screw, $B_d$, flowing into an inclined reactor ($B_i$) with liquid $L_B$ being removed.

The biomass, now soaked and washed for the second time, is sent to a third soaking zone, Zone C, being characterized similarly as Zones A and B. In the case of Zone C, the steam entering the soaking zone C is at a Temperature $T_3$ and Pressure $P_3$, with biomass being kept in the zone at temperature $T_C$ and for a time, $t_C$. The biomass moves through a discharge screw, $C_d$, flowing into an inclined reactor ($C_i$) with liquid $L_C$ being removed.

The biomass is then moved to a compressor to prepare it for steam explosion. The last zone is to have its severity higher than the severity of at least one of the zones before it in the process.

The process could also be done in a single vertical reactor comprised of zones, such as those described in US 2008/0295981, (See FIG. 1 of US 2008/0295981).

Figure 2:
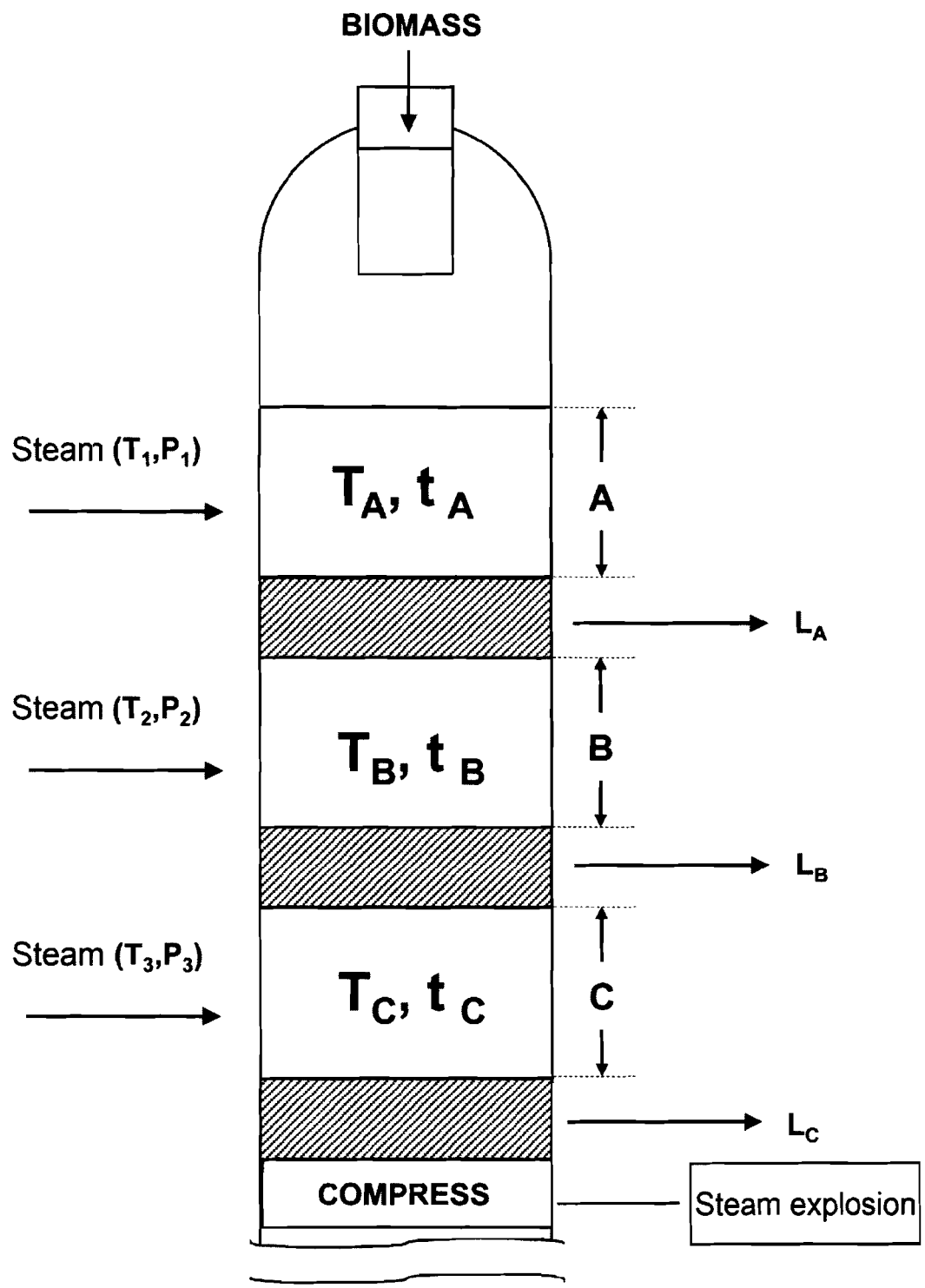
FIG. 2 is a schematic of a second embodiment of the process.

The adaption to the vertical column is readily apparent once one of ordinary skill realizes that multiple washes in progressive temperature is beneficial. FIG. 2 of this specification demonstrates the unit operations of such a device. The biomass is fed into the top of the vessel passing into Zone A, where the biomass is treated at mild temperature conditions in the presence of steam introduced at temperature $T_1$ and pressure $P_1$ and biomass held at temperature $T_A$ for a set period time $t_A$, having generally a low severity. The liquid, $L_A$, containing xylan can be separated from the biomass using an extraction screen indicated by the diagonal lines underneath Zone A or some other device and the solids passed into the next Zone, Zone B.

In Zone B the biomass is treated in the presence of steam introduced at temperature $T_2$ and pressure $P_2$ and biomass held at temperature $T_B$ for a set period time $t_B$, and the liquid, $L_B$, containing xylan is separated from the biomass the using an extraction screen indicated by the diagonal lines underneath Zone B or some other device and the solids passed into the next Zone, Zone C.

In Zone C the biomass is treated in the presence of steam introduced at temperature $T_3$ and pressure $P_3$ and biomass held at temperature $T_C$ for a set period time, $t_C$, and the liquid, $L_C$, containing xylan can be separated from the biomass using an extraction screen indicated by the diagonal lines underneath Zone C or some other device and the solids passed into the next Zone, or in this case, the compression step in preparation for steam explosion.

It is preferred to have the severity increase with each soaking.

After the washing steps are completed, the liquid streams can be collected and further treated. The solid biomass is then recovered and usually passed onto a steam explosion step, which could be mounted at the bottom of the vertical reactor.

In the above embodiment, the material flow is downward. However, the flow could also be upward with the liquid extraction device different so that the liquid, usually water, moves countercurrent to the flow of the biomass. The zones can be configured horizontal to each other and the biomass would thus move sideways.

According to a further embodiment of the invention, at least one of the wash steps has a severity greater than or equal to the severity of a previous wash step in the process.

The process may run as a continuous process or batch process.

It should be apparent from the examples and embodiments that this invention is not limited to the embodiments as many variations of the invention exist.

The invention claimed is:

1. A process for the soaking of lignocellulosic biomass, comprising the steps of
   A) introducing a lignocellulosic biomass feedstock into a first soaking zone,
   B) soaking the lignocellulosic biomass feedstock in the presence of a liquid or vapor of the liquid for a first time and a first temperature correlating to a first severity of the soaking conditions creating a first liquid comprised of at least one compound selected from the group consisting of xylose and soluble oligomers thereof,
   C) separating at least a portion of the first liquid comprised of the at least one compound selected from the group consisting of xylose and soluble oligomers thereof from the biomass of the first soaking,
   D) introducing the biomass of the first soaking zone into a second soaking zone in the presence of a liquid for a second time and a second temperature correlating to a second severity of the soaking conditions creating a second liquid comprised of at least one compound selected from the group consisting of xylose and soluble oligomers thereof wherein the second severity is greater than first severity,
   E) separating at least a portion of the second free liquid comprised of the at least one compound selected from the group consisting of xylose and soluble oligomers thereof from the biomass of the second soaking,
   F) moving the biomass of the second soaking zone into a compressor to prepare the biomass for steam explosion, and
   G) moving the biomass from the compressor to a steam explosion device.

2. The process according to claim 1, wherein the soaking of each soaking zone is conducted in a separate vessel.

3. The process according to claim 1, wherein the soaking zones are in a single vessel and the first soaking zone is positioned above the second soaking zone.

4. The process according to claim 1, wherein the soaking zones are in a single vessel and first soaking zone and second soaking zone are horizontal to each other.

5. The process according to claim 1, wherein the soaking zones are in a single vessel and the first soaking zone is located beneath the second soaking zone.

6. The process according to claim 1, comprising the further steps of, after separating at least a portion of the second free liquid and before moving the biomass of the second soaking zone into the compressor, introducing the biomass from the second soaking zone into a third soaking zone in the presence of a liquid for a third time and at a third temperature range correlating to a third severity of the soaking conditions creating a third liquid comprised of at least one compound selected from the group consisting of xylose and soluble oligomers thereof wherein the third severity is greater than second severity, and separating at least a portion of the third liquid comprised of at least one compound selected from the group consisting of xylose and soluble oligomers thereof from the biomass of the third soaking.

7. The process according to claim 2, wherein the soaking of each soaking zone is conducted in a separate vessel.

8. The process according to claim 2, wherein the soaking zones are in a single vessel and the first soaking zone is positioned above the second soaking zone.

9. The process according to claim 2, wherein the soaking zones are in a single vessel and first soaking zone and second soaking zone are horizontal to each other.

10. The process according to claim 2, wherein the soaking zones are in a single vessel and the first soaking zone is located beneath the second soaking zone.

* * * * *